US007756365B2

(12) United States Patent
Cunningham et al.

(10) Patent No.: US 7,756,365 B2
(45) Date of Patent: Jul. 13, 2010

(54) NEAR ULTRAVIOLET-WAVELENGTH PHOTONIC-CRYSTAL BIOSENSOR WITH ENHANCED SURFACE TO BULK SENSITIVITY RATIO

(75) Inventors: Brian T. Cunningham, Champaign, IL (US); Nikhil Ganesh, Champaign, IL (US); Ian D. Block, Champaign, IL (US)

(73) Assignees: University of Illinois, Urbana, IL (US); SRU Biosystems, Inc., Woburn, MA (US)

(*) Notice: Subject to any disclaimer, the term of this patent is extended or adjusted under 35 U.S.C. 154(b) by 439 days.

(21) Appl. No.: 11/822,303

(22) Filed: Jul. 2, 2007

(65) Prior Publication Data
US 2008/0014632 A1    Jan. 17, 2008

Related U.S. Application Data

(60) Provisional application No. 60/819,436, filed on Jul. 7, 2006.

(51) Int. Cl.
*G02B 6/00* (2006.01)
(52) U.S. Cl. .................. 385/12; 385/147; 435/287.2
(58) Field of Classification Search .............. 385/10, 385/12, 13, 37, 129, 147; 435/287.2
See application file for complete search history.

(56) References Cited

U.S. PATENT DOCUMENTS

| 7,094,595 | B2* | 8/2006 | Cunningham et al. ..... 435/287.2 |
| 7,162,125 | B1 | 1/2007 | Schulz ...................... 385/37 |
| 7,197,198 | B2* | 3/2007 | Schulz et al. ................. 385/12 |
| 2002/0127565 | A1 | 9/2002 | Cunningham et al. .......... 435/6 |
| 2003/0017581 | A1 | 1/2003 | Li et al. ................... 435/287.2 |
| 2003/0027327 | A1 | 2/2003 | Cunningham et al. ..... 435/287.2 |
| 2003/0032039 | A1 | 2/2003 | Cunningham et al. .......... 435/6 |
| 2003/0059855 | A1 | 3/2003 | Cunningham et al. ........ 435/7.9 |
| 2003/0077660 | A1 | 4/2003 | Pien et al. ................... 435/7.1 |
| 2006/0024013 | A1* | 2/2006 | Magnusson et al. .......... 385/129 |
| 2007/0009968 | A1 | 1/2007 | Cunningham et al. ........ 435/7.9 |

FOREIGN PATENT DOCUMENTS

WO    WO 2007/019024    2/2007

OTHER PUBLICATIONS

International Preliminary Report on Patentability in PCT/US2007/015448, mailed Jan. 22, 2009.
Nano Sensors Group, "Nano Sensors Group in the News", Department of Electrical and Computer Engineering, University of Illinois, on-line press release dated Jul. 7, 2006.

(Continued)

*Primary Examiner*—Akm E Ullah
(74) *Attorney, Agent, or Firm*—McDonnell Boehnen Hulbert & Berghoff LLP

(57) ABSTRACT

Biosensors are disclosed based on one- or two-dimensional photonic-crystal reflectance filters operating at near-ultraviolet wavelengths. The biosensors feature a tightly confined resonant electric field at the surface of this biosensor and provide a high surface-sensitivity to bulk-sensitivity ratio, and therefore enables enhanced detection resolution for biomolecules adsorbed on the biosensor surface. These new biosensors can be fabricated in mass by replica molding. They are especially well suited for applications requiring the detection of small molecules or ultra-low analyte concentrations.

16 Claims, 5 Drawing Sheets

OTHER PUBLICATIONS

Moharam et al., "Rigorous coupled-wave analysis of planar-grating diffraction", Optical Society of America, vol. 71, No. 7, pp. 811-818 (1981).

Wang et al., "Guided-mode resonances in planar dielectric-layer diffraction gratings", Optical Society of America, A/vol. 7, No. 8, pp. 1470-1474 (1990).

Wang et al., "Theory and applications of guided-mode resonance filters", Applied Optics, vol. 32, No. 14, pp. 2606-2613 (May 10, 1993).

Malmqvist et al., "Biomolecular interaction analysis: affinity biosensor technologies for functional analysis of proteins", Curr. Opin. Chem. Biol. 1, pp. 378-383 (1997).

A. J. Cunningham, "Optically Based Energy Transduction", Introduction to Bioanalytical Sensors, Chapter 5, pp. 260-295, John Wiley & Sons, New York (1998).

Myszka et al., "Implementing surface Plasmon resonance biosensors in drug discovery", Pharm. Sci. Tech. Today vol. 3, No. 9, pp. 310-317 (2000).

Cunningham et al., "Colorimetric resonant reflection as a direct biochemical assay technique", Sensors and Actuators B, 81 (2002) p. 316-328.

Cunningham, et al., "A plastic colorimetric resonant optical biosensor for multiparallel detection of label-free biochemical interactions", Sensors and Actuators B, vol. 85, pp. 219-226 (2002).

Haes et al., "A Nanoscale Optical Biosensor: Sensitivity and Selectivity of an Approach Based on the Localized Surface Plasmon Resonance Spectroscopy of Triangular Silver Nanoparticles", Journal of the American Chemical Society, vol. 124, pp. 10596-10604 (2002).

Li et al., "A new method for label-free imaging of biomolecular interactions", Sensors and Actuators B, vol. 99, pp. (2003).

Cunningham et al., "Label-Free Assays on the BIND System", The Society for Biomolecular Screening 9, pp. 481-490 (2004).

Block et al., "Photonic crystal optical biosensor incorporating structured low-index porous dielectric", Sensors and Actuators B, vol. 120, pp. 187-193 (2006).

Ganesh et al., "Photonic-crystal near-ultraviolet reflectance filters fabricated by nonoreplica molding", Applied Physics Letters, vol. 88, No. 7, pp. 0711101-0711103 (2006).

Block et al., *Photonic Crystal Optical Biosensor Incorporating Structured Low-Index Porous Dielectric*, IEEE Sensors, XP-002461573, pp. 742-745 (2005).

Ganesh et al., *Photonic-crystal near-ultraviolet reflectance filters fabricated by nanoreplica molding*, Applied Physics Letters vol. 88, No. 7, pp. 07-1110-1-3 (Feb. 14, 2006).

Ganesh et al., *Fabrication and Characterization of High Sensitivity Visible Light Photonic Crystal Biosensors*, Proc. Progress in Electromagnetics Research Symposium, , Session 2A2, Plasmonic Nanophotonics (Mar. 26-29, 2006).

PIERS 2006 Cambridge-upload presentation files XP002461572, URL:http://emacademy.org/piers Session A2 , Plasmonic Nanophotonics (2006).

Ganesh et al., *Near ultraviolet-wavelength photonic-crystal biosensor with enhanced surface-to-bulk sensitivity ratio*, Applied Physics Letters, vol. 89, No. 2, pp. 023901-1-3 (Jul. 10, 2006).

International Search Report and Written Opinion in PCT/US2007/015448, dated Dec. 19, 2007.

\* cited by examiner

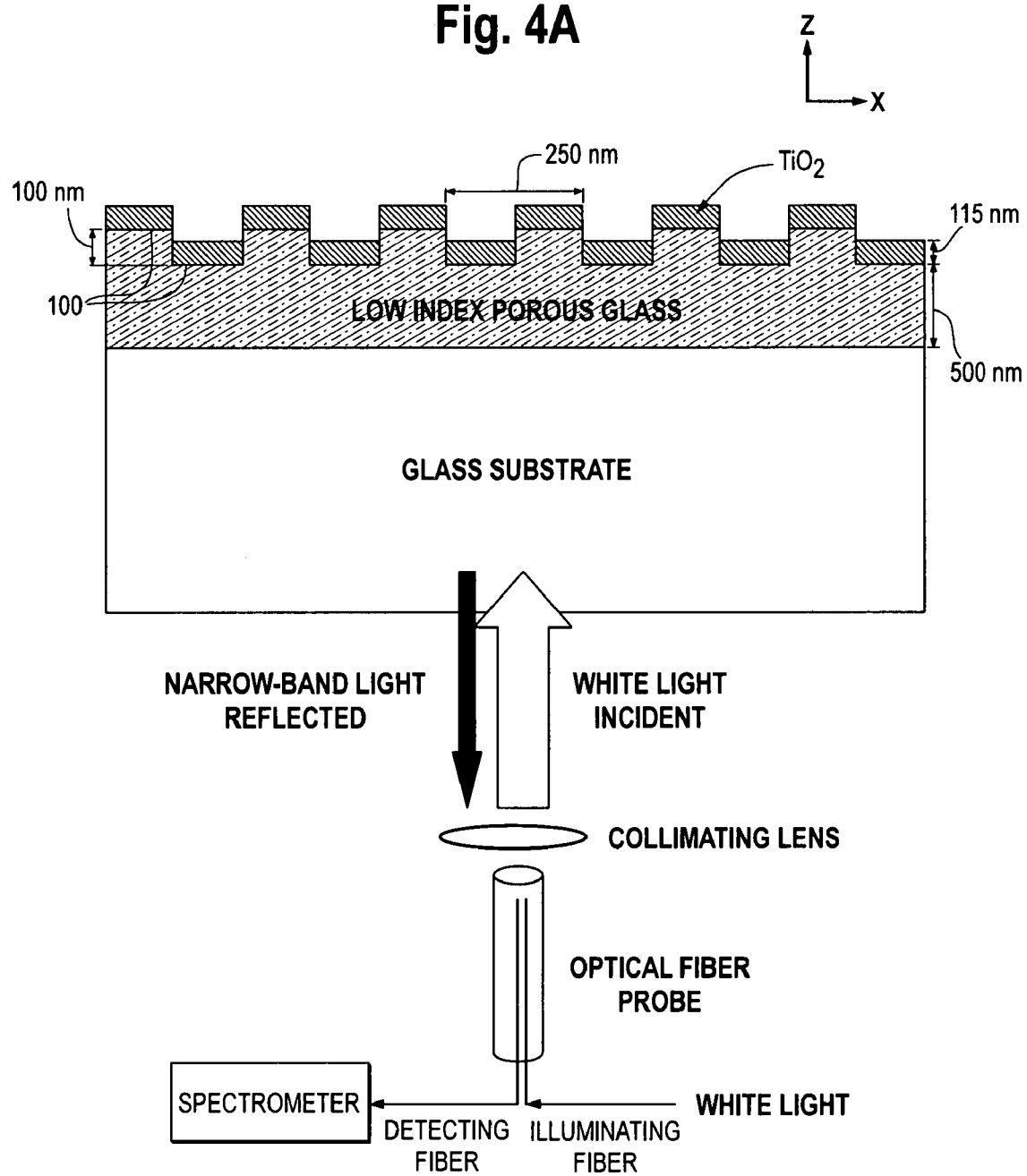

NEAR ULTRAVIOLET-WAVELENGTH PHOTONIC-CRYSTAL BIOSENSOR WITH ENHANCED SURFACE TO BULK SENSITIVITY RATIO

This application claims priority under 35 U.S.C. §119(e) to U.S. Provisional Application Ser. No. 60/819,436 filed Jul. 7, 2006, the content of which is incorporated by reference herein.

STATEMENT REGARDING FEDERALLY SPONSORED RESEARCH

The U.S. Government has a paid-up license in this invention and the right in limited circumstances to require the patent owner to license others on reasonable terms as provided for by the terms of grant no. BES 0427657 from the National Science Foundation.

BACKGROUND

A. Field of the Invention

This invention relates generally to grating-based biochemical sensor devices. Such devices are typically based on photonic crystal technology and are used for optical detection of the adsorption of a biological material, such as DNA, protein, viruses or cells, or chemicals, onto a surface of the device or within a volume of the device. More particularly, this disclosure relates to a new device design which is especially useful for detection of small molecules or low concentrations of analytes which are deposited on the surface of the biosensor.

B. Description of Related Art

Grating-based biosensors represent a new class of optical devices that have been enabled by recent advances in semiconductor fabrication tools with the ability to accurately deposit and etch materials with precision less than 100 nm.

Several properties of photonic crystals make them ideal candidates for application as grating-type optical biosensors. First, the reflectance/transmittance behavior of a photonic crystal can be readily manipulated by the adsorption of biological material such as proteins, DNA, cells, virus particles, and bacteria. Each of these types of material has demonstrated the ability to alter the optical path length of light passing through them by virtue of their finite dielectric permittivity. Second, the reflected/transmitted spectra of photonic crystals can be extremely narrow, enabling high-resolution determination of shifts in their optical properties due to biochemical binding while using simple illumination and detection apparatus. Third, photonic crystal structures can be designed to highly localize electromagnetic field propagation, so that a single photonic crystal surface can be used to support, in parallel, the measurement of a large number of biochemical binding events without optical interference between neighboring regions within <3-5 microns. Finally, a wide range of materials and fabrication methods can be employed to build practical photonic crystal devices with high surface/volume ratios, and the capability for concentrating the electromagnetic field intensity in regions in contact with a biochemical test sample. The materials and fabrication methods can be selected to optimize high-volume manufacturing using plastic-based materials or high-sensitivity performance using semiconductor materials.

Representative examples of grating-type biosensors in the prior art are disclosed in Cunningham, B. T., P. Li, B. Lin, and J. Pepper, *Colorimetric resonant reflection as a direct biochemical assay technique*. Sensors and Actuators B, 2002. 81: p. 316-328; Cunningham, B. T., J. Qiu, P. Li, J. Pepper, and B. Hugh, *A plastic calorimetric resonant optical biosensor for multiparallel detection of label-free biochemical interactions*, Sensors and Actuators B, 2002. 85: p. 219-226; Haes, A. J. and R. P. V. Duyne, *A Nanoscale Optical Biosensor: Sensitivity and Selectivity of an Approach Based on the Localized Surface Plasmon Resonance Spectroscopy of Triangular Silver Nanoparticles*. Journal of the American Chemical Society, 2002. 124: p. 10596-10604.

The combined advantages of photonic crystal biosensors may not be exceeded by any other label-free biosensor technique. The development of highly sensitive, miniature, low cost, highly parallel biosensors and simple, miniature, and rugged readout instrumentation will enable biosensors to be applied in the fields of pharmaceutical discovery, diagnostic testing, environmental testing, and food safety in applications that have not been economically feasible in the past.

In order to adapt a photonic bandgap device to perform as a biosensor, some portion of the structure must be in contact with a liquid test sample. Biomolecules, cells, proteins, or other substances are introduced to the portion of the photonic crystal and adsorbed where the locally confined electromagnetic field intensity is greatest. As a result, the resonant coupling of light into the crystal is modified, and the reflected/transmitted output (i.e., peak wavelength) is tuned, i.e., shifted. The amount of shift in the reflected output is related to the amount of substance present on the sensor. The sensors are used in conjunction with an illumination and detection instrument that directs polarized light into the sensor and captures the reflected or transmitted light. The reflected or transmitted light is fed to a spectrometer that measures the shift in the peak wavelength.

The ability of photonic crystals to provide high quality factor (Q) resonant light coupling, high electromagnetic energy density, and tight optical confinement can also be exploited to produce highly sensitive biochemical sensors. Here, Q is a measure of the sharpness of the peak wavelength at the resonant frequency. Photonic crystal biosensors are designed to allow a liquid test sample to penetrate the periodic lattice, and to tune the resonant optical coupling condition through modification of the surface dielectric constant of the crystal through the attachment of biomolecules or cells. Due to the high Q of the resonance, and the strong interaction of coupled electromagnetic fields with surface-bound materials, several of the highest sensitivity biosensor devices reported are derived from photonic crystals. See the Cunningham et al. papers cited previously. Such devices have demonstrated the capability for detecting molecules with molecular weights less than 200 Daltons (Da) with high signal-to-noise margins, and for detecting individual cells. Because resonantly-coupled light within a photonic crystal can be effectively spatially confined, a photonic crystal surface is capable of supporting large numbers of simultaneous biochemical assays in an array format, where neighboring regions within ~10 µm of each other can be measured independently. See Li, P., B. Lin, J. Gerstenmaier, and B. T. Cunningham, *A new method for label-free imaging of biomolecular interactions*. Sensors and Actuators B, 2003.

There are many practical benefits for biosensors based on photonic crystal structures. Direct detection of biochemical and cellular binding without the use of a fluorophore, radio-ligand or secondary reporter removes experimental uncertainty induced by the effect of the label on molecular conformation, blocking of active binding epitopes, steric hindrance, inaccessibility of the labeling site, or the inability to find an appropriate label that functions equivalently for all molecules in an experiment. Label-free detection methods greatly simplify the time and effort required for assay development, while removing experimental artifacts from quenching, shelf life, and background fluorescence. Compared to other label-free optical biosensors, photonic crystals are easily queried by simply illuminating at normal incidence with a broadband light source (such as a light bulb or LED) and measuring shifts in the reflected color. The simple excitation/readout scheme enables low cost, miniature, robust systems that are suitable for use in laboratory instruments as well as portable handheld systems for point-of-care medical diagnostics and environmental monitoring. Because the photonic crystal itself consumes no power, the devices are easily embedded within a variety of liquid or gas sampling systems, or deployed in the context of an optical network where a single illumination/detection base station can track the status of thousands of sensors within a building. While photonic crystal biosensors can be fabricated using a wide variety of materials and methods, high sensitivity structures have been demonstrated using plastic-based processes that can be performed on continuous sheets of film. Plastic-based designs and manufacturing methods will enable photonic crystal biosensors to be used in applications where low cost/assay is required, that have not been previously economically feasible for other optical biosensors.

Photonic crystal biosensors and associated detection instruments are described in the patent literature; see U.S. patent application publications U.S. 2003/0027327; 2002/0127565, 2003/0059855 and 2003/0032039. Methods for detection of a shift in the resonant peak wavelength are taught in U.S. Patent application publication 2003/0077660. The biosensor described in these references include 1- and 2-dimensional periodic structured surfaces applied to a continuous sheet of plastic film or substrate. The crystal resonant wavelength is determined by measuring the peak reflectivity at normal incidence with a spectrometer to obtain a wavelength resolution of 0.5 picometer. The resulting mass detection sensitivity of <1 $pg/mm^2$ (obtained without 3-dimensional hydrogel surface chemistry) has not been demonstrated by any other commercially available biosensor.

A fundamental advantage of the biosensor devices described in the above-referenced patent applications is the ability to mass-manufacture with plastic materials in continuous processes at a 1-2 feet/minute rate. Methods of mass production of the sensors are disclosed in U.S. Patent application publication 2003/0017581.

As shown in FIG. 1, the periodic surface structure of a prior art near-IR biosensor 10 is fabricated from a low refractive index material 12 that is overcoated with a thin film of higher refractive index material 14. The low refractive index material 12 is bonded to a substrate 16. The surface structure is replicated within a layer of cured epoxy 12 from a silicon-wafer "master" mold (i.e. a negative of the desired replicated structure) using a continuous-film process on a polyester substrate 16. The liquid epoxy 12 conforms to the shape of the master grating, and is subsequently cured by exposure to ultraviolet light. The cured epoxy 12 preferentially adheres to the polyester substrate sheet 16, and is peeled away from the silicon wafer. Sensor fabrication was completed by sputter deposition of 120 nm titanium oxide ($TiO_2$) high index of refraction material 14 on the cured epoxy 12 grating surface. Following titanium oxide deposition, 3×5-inch microplate sections are cut from the sensor sheet, and attached to the bottoms of bottomless 96-well and 384-well microtiter plates with epoxy.

As shown in FIG. 2, the wells 20 defining the wells of the microtiter plate contain a liquid sample 22. The combination of the bottomless microplate and the biosensor structure 10 is collectively shown as biosensor apparatus 26. Using this approach, photonic crystal sensors are mass produced on a square-yardage basis at very low cost.

The detection instrument for the photonic crystal biosensor is simple, inexpensive, low power, and robust. A schematic diagram of the system is shown in FIG. 2. FIG. 3 is an illustration of an arrangement of 8 illumination heads that read an entire row of wells of a biosensor device comprising the structure of FIG. 1 affixed to the bottom of a bottomless microtiter plate. In order to detect the reflected resonance, a white light source illuminates a ~1 mm diameter region of the sensor surface through a 100 micrometer diameter fiber optic 32 and a collimating lens 34 at nominally normal incidence through the bottom of the microplate. A detection fiber 36 is bundled with the illumination fiber 32 for gathering reflected light for analysis with a spectrometer 38. A series of 8 illumination/detection heads 40 are arranged in a linear fashion, so that reflection spectra are gathered from all 8 wells in a microplate column at once. The microplate+biosensor 10 sits upon a X-Y addressable motion stage (not shown in FIG. 2) so that each column of wells in the microplate can be addressed in sequence. The instrument measures all 96 wells in ~15 seconds, limited by the rate of the motion stage. Further details on the construction of the system of FIGS. 2 and 3 are set forth in the published U.S. Patent Application 2003/0059855.

Other references of interest includes: D. G. Myszka and R. L. Rich, Pharm. Sci. Technol. Today 3, 310 (2000); M. Malmqvist and R. Karlsson, Curr. Opin. Chem. Biol. 1, 378 (1997); B. Cunningham, B. Lin, J. Qiu et al., Sens. and Act. B 85 (3), 219 (2002); B. T. Cunningham, P. Li, S. Schulz et al., J. Biomol. Screen 9, 481-490 (2004); I. D. Block, L. L. Chan, and B. T. Cunningham, "Photonic Crystal Optical Biosensor Incorporating Structured Low-Index Porous Dielectric," Sensors and Actuators, B: Chemical, v 120, n 1, Dec. 14, 2006, p 187-193; S. S. Wang, R. Magnusson, and J. S. Bagby, J. Opt. Soc. Am. A 7 (8), 1470-1474 (1990); S. S. Wang and R. Magnusson, Applied Optics 32, 2606 (1993); N. Ganesh and B. T. Cunningham, "Photonic Crystal Near UV Reflectance Filters Fabricated by Nano Replica Molding", Applied Physics Letters, v. 88, n. 7, pp. 071110-071113 (2006); M. G. Moharam and T. K. Gaylord, J. Opt. Soc. Am. 71, 811-818 (1981). Prior art status of all of the above references is not admitted.

All of the previously cited art is fully incorporated by reference herein.

SUMMARY

This invention is directed to biosensors based on photonic-crystals having a surface grating structure exhibiting a peak wavelength value in the near-ultraviolet wavelengths. Such biosensors are characterized in having a more tightly confined resonant electric field in response to incident light at the surface of this biosensor as compared to previously fabricated near-infrared photonic-crystal biosensors. This change in the resonant electric field, i.e., more tightly confined at the surface of the biosensor, provides an improvement of over 4.5 times in terms the ratio of the surface-sensitivity of the biosensor to the bulk-sensitivity of the biosensor as compared to a prior art photonic crystal biosensor exhibiting a peak wavelength value in the near-infrared. Accordingly, the photonic crystal biosensor of this invention enables enhanced detection resolution for biomolecules, small molecules, or other analytes in low or ultra low concentrations which are adsorbed on the biosensor surface. The biosensors of this disclosure are a significant step forward towards the ultimate goal of a biosensor capable of single molecule resolution.

For photonic crystals of the type of this disclosure, the spectral location of peak reflection, or peak-wavelength value (PWV), is readily tuned by changes in the optical density of the medium deposited on the sensor grating surface lying within the range of the evanescent electric field. Therefore, bulk refractive index (RI) changes of the cover medium will induce a shift in the PWV, as will any thickness or density changes of a surface-bound biomolecular layer. Since bulk solution RI variations are a significant source of noise for surface-based optical biosensors, a higher ratio of surface-to-bulk sensitivity will consequently yield enhanced detection resolution. Accordingly, the biosensor designs of this disclosure maximize the PWV shift in response to a given biomolecular monolayer which is deposited on the surface of the biosensor, while simultaneously limiting sensitivity to RI variations of the bulk media.

In one aspect, a photonic crystal biosensor takes the form of an optically transparent substrate, and a relatively low index of refraction material formed in a periodic grating structure applied to the substrate. The low index of refraction material may optionally take the form of a porous dielectric material such as a spin-on glass, such as Honeywell "NANO-GLASS"™. A relatively high index of refraction material (e.g., $TiO_2$) is deposited onto the low index of refraction grating structure. The grating structure period and physical structure, and the thickness of the high index of refraction material, are selected such that the sensor produces a substantial confinement of the electric field intensity due to light directed to the biosensor substantially at the surface of the periodic grating. An example of such confinement is demonstrated for a one-dimensional periodic surface grating in FIG. 4A. Furthermore, a reflection maximum at a resonant wavelength of the biosensor occurs in the near-ultraviolet portion of the spectrum (e.g., λ approximately in the range of 280-525 nm). Additionally, the biosensor grating structure and high and low index of refraction materials are selected to result in a biosensor which has a relatively high surface to bulk sensitivity ratio thereby improving the ability of the device to detect low concentrations of biomolecules, analytes, and/or and small molecules deposited on the surface of the biosensor.

In one embodiment, the biosensor has a surface to bulk sensitivity ratio of approximately 0.060 or higher. In another embodiment, the biosensor has a bulk shift coefficient of approximately 100 nm/refractive index units (RIU) or less and has a surface sensitivity measured by surface-absorbed material of PPL (poly-phe-lysine) of approximately 3 nm or greater. The bulk shift coefficient is defined as the $\Delta PWV/\Delta n$, where $\Delta PWV$ is change in the resonance wavelength due to placement of a bulk medium on the surface of the biosensor, and where $\Delta n$ is the change in the refractive index due to the bulk medium applied to the surface of the biosensor.

In one embodiment, the grating structure comprises a one-dimensional surface structure. In other embodiments, the grating structure comprises a two-dimensional surface grating structure. The two-dimensional surface grating structure may comprise a two-dimensional array of posts or holes, arranged in a rectangular array, a hexagonal lattice, or other format. The posts or holes can have a variety of desired shapes, such as square, rectangular, circular, ovoid, triangular, etc.

In another aspect, a method is disclosed of fabricating a highly sensitive biosensor comprising the steps of: a) conducting a nanoreplication process by which a relatively low index of refraction material is patterned on an optically transparent substrate as a periodic surface grating structure; b) depositing a relatively high index of refraction material onto the periodic surface grating structure; c) wherein the grating structure period and physical structure, and high and low index of refraction materials are selected, such that the sensor produces a substantial confinement of the electric field intensity due to light directed to the biosensor substantially at the surface of the periodic grating and wherein a reflection maximum at a resonant wavelength occurs in the near-ultraviolet portion of the spectrum, d) and further wherein the sensor grating structure period and high and low index of refraction materials are selected to result in a biosensor which has a relatively high surface to bulk sensitivity ratio thereby improving the ability of the biosensor to detect low concentrations of biomolecules, analytes, and/or and small molecules deposited on the surface of the biosensor.

In another aspect, a system is provided for detection of low concentrations of biomolecules, analytes, and/or and small molecules, comprising in combination: a biosensor as described above, wherein the biomolecules, analytes and/or small molecules are deposited on the surface of the biosensor, and a detection instrument for illuminating the biosensor and measuring a shift in the peak wavelength value of reflected light from the surface of the biosensor, the shift in peak wavelength value due to the presence of the low concentration of the biomolecules, analytes and/or small molecules deposited on the surface of the biosensor.

BRIEF DESCRIPTION OF THE DRAWINGS

FIG. 4A is a cross-sectional illustration of a one-dimensional periodic surface structure as replicated into the low refractive index (RI) porous spin-on glass, which is formed on the surface of an optically transparent substrate material. The period of the structure is ~250 nm. Upon coating of this structure with high RI $TiO_2$, the final biosensor device is obtained.

DETAILED DESCRIPTION

Figure 1:
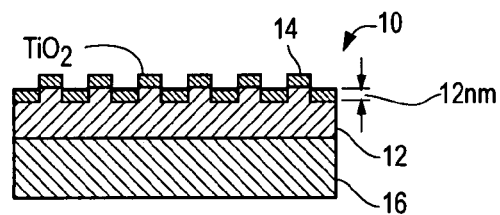
FIG. 1 is an illustration of a prior art biosensor arrangement.
Figure 2:
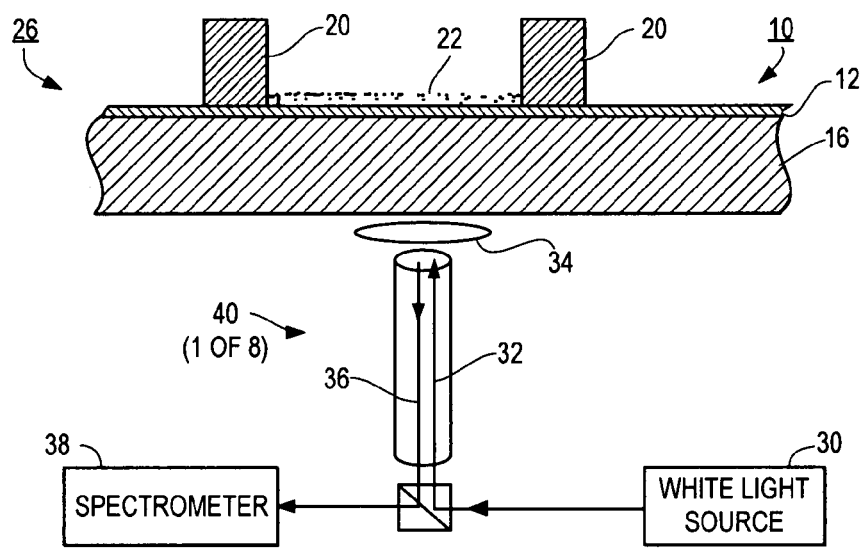
FIG. 2 is an illustration of a prior art biosensor and detection system for illuminating the biosensor and measuring shifts in the peak wavelength of reflected light from the biosensor.
Figure 3:
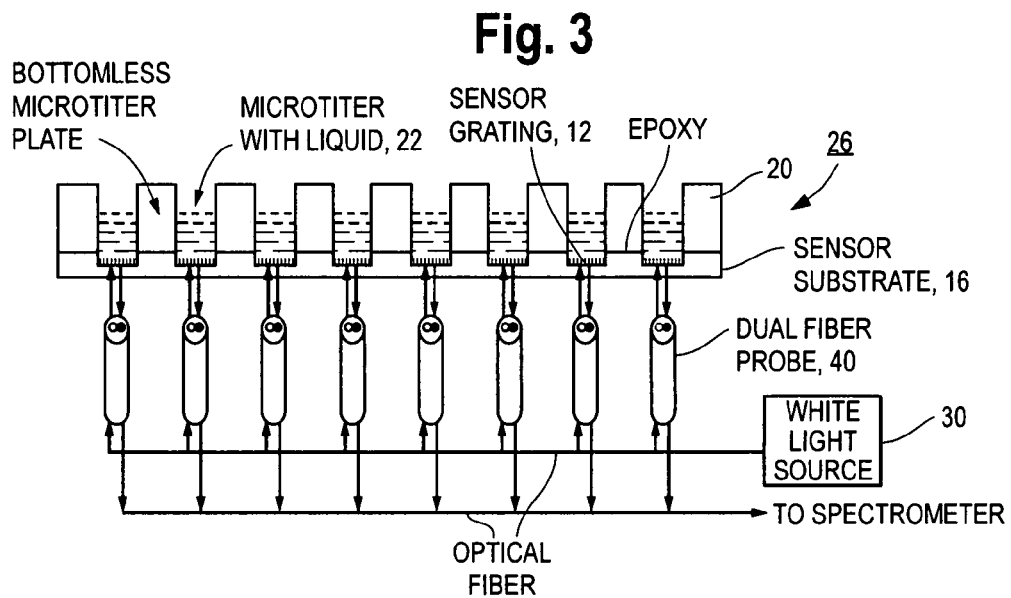
FIG. 3 is an illustration of an arrangement of 8 illumination heads that read an entire row of wells of a biosensor device comprising the structure of FIG. 1 affixed to the bottom of a bottomless microtiter plate.

Biosensors are descried below which are based on one- or two-dimensional photonic-crystals operating at near-ultraviolet wavelengths. Rigorous Coupled-Wave Analysis simulations of the biosensors predict a more tightly confined resonant electric field at the surface of this biosensor as compared to previously fabricated near-infrared photonic-crystal biosensors. This change in the resonant electric field provides an improvement of over 4.5 times in the surface-sensitivity to bulk-sensitivity ratio, and therefore enables enhanced detection resolution for biomolecules adsorbed on the biosensor surface. These new biosensors fabricated by replica molding will be especially important for applications requiring the detection of small molecules or ultra-low analyte concentrations.

There is a growing interest in biomolecular detection platforms for drug discovery, environmental detection, medical diagnostics and life science research. See the Myszka et al. and Malqvist et al. articles cited previously. Traditional labeled detection methods can introduce significant experimental complexity, uncertainty, and cost. Label-free biosensors are an important emerging class of sensors that circumvent these limitations and can reveal binding affinity, specificity, and kinetics. See A. J. Cunningham, *Introduction to Bioanalytical Sensors* (John Wiley & Sons, New York, 1998) p. 418.

A novel near-infrared (n-IR) photonic-crystal (PC) optical biosensor has previously been demonstrated (see B. Cunningham, B. Lin, J. Qiu et al., Sens. and Act. B 85 (3), 219 (2002)) for label-free detection of biochemical interactions, exhibiting a mass density sensitivity resolution of less than 1 $pg/mm^2$, refractive index discrimination down to $10^{-6}$ refractive index units (RIU), and a large dynamic range. B. T. Cunningham, P. Li, S. Schulz et al., J. Biomol. Screen 9, 481-490 (2004). Recently, we have discovered that by substituting a low refractive index (RI) porous dielectric for the UV-cured polymer used in previous designs, the sensitivity of the PC biosensor is significantly enhanced. I. D. Block, L. L. Chan, and B. T. Cunningham, "Photonic Crystal Optical Biosensor Incorporating Structured Low-Index Porous Dielectric," Sensors and Actuators, B: Chemical, v 120, n 1, Dec. 14, 2006, p 187-193. In the present disclosure we demonstrate the scaling of this process to report the first near-ultraviolet (n-UV) PC biosensors.

The label-free PC optical biosensor uses an optically transparent substrate and a low refractive index nanostructure onto which a high refractive index material is deposited, as shown in FIG. 4A. The device is designed as a narrow-band reflectance filter with unity reflection efficiency at band center, the precise reflection characteristics governed by the height and period of the surface structure, the thickness of the high index ($TiO_2$) layer and the strength of modulation (RI difference of the materials). The reflection arises by utilizing a guided-mode resonance effect, in which a structured surface incorporates a sub-wavelength periodic dielectric permittivity modulation.

For the resonant wavelength, only the zero-order forward and backward-diffracted waves are coupled to the structure, with all higher-order waves cut off, theoretically resulting in 100% reflection efficiency. The reflection maximum for the n-IR and n-UV biosensors is centered at 795 nm and 405 nm respectively. The design and fabrication of plastic n-UV PC reflectance filters has been described in our prior work (see N. Ganesh and B. T. Cunningham, "Photonic Crystal Near UV Reflectance Filters Fabricated by Nano Replica Molding", Applied Physics Letters, v. 88, n. 7, pp. 071110-071113 (2006)) and the process therein is extended to a low RI porous dielectric to fabricate these n-UV biosensors.

One-Dimensional Example

Figure 4B:
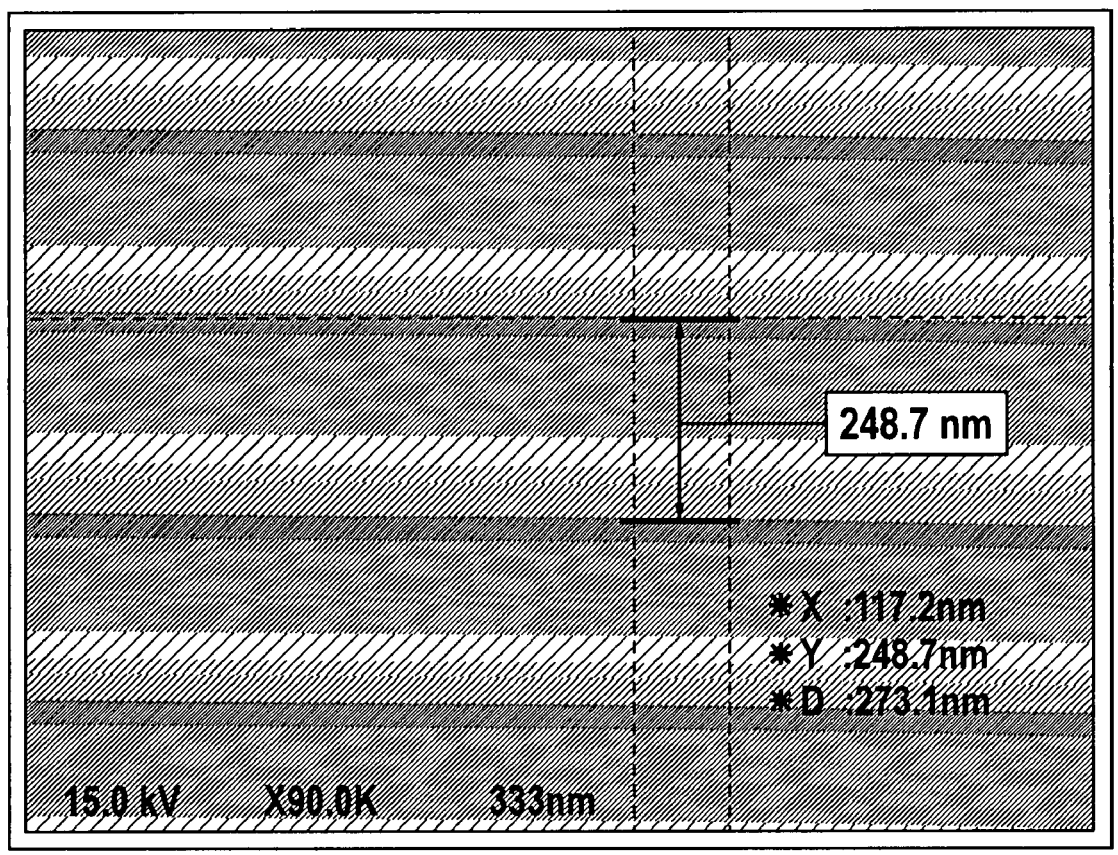
FIG. 4B is a scanning electron microscopy image of the structure of FIG. 4A.

A one-dimensional surface structure (period=250 nm) is patterned in a $Si/SiO_2$/poly (methylmethacrylate) substrate by electron-beam lithography and etched into the $SiO_2$ using reactive ion etching. This structure is used as a 'master' mold from which a stamp in polydimethylsiloxane (PDMS) is prepared. This PDMS stamp is used in a nanoreplication process, to in turn pattern a glass substrate coated with a low RI spin-on glass (Nanoglass, Honeywell). This structure is shown in FIG. 4A. Finally, a layer of high RI $TiO_2$ is evaporated onto this structure to obtain the biosensor device. FIG. 4B shows the structure as imaged by a scanning electron microscope.

The grating structure period and physical structure, and the thickness of the high index of refraction material, are selected such that the sensor produces a substantial confinement of the electric field intensity due to light directed to the biosensor substantially at the plane of the periodic surface grating of the biosensor. An example of such confinement is demonstrated for a one-dimensional periodic surface grating in FIG. 5A. FIG. 5B shows the confinement of the electric field for a near-IR sensor, for purposes of comparison. Furthermore, a reflection maximum at a resonant wavelength of the biosensor occurs in the near-ultraviolet portion of the spectrum (e.g., λ approximately in the range of 280-525 nm, in this particular case 405 nm). Additionally, the biosensor grating structure and high and low index of refraction materials are selected to result in a biosensor which has a relatively high surface to bulk sensitivity ratio thereby improving the ability of the device to detect low concentrations of biomolecules, analytes, and/or and small molecules deposited on the surface of the biosensor.

The spectral location of peak reflection, or peak-wavelength value (PWV), is readily tuned by changes in the optical density of the medium atop the sensor surface lying within the range of the evanescent electric field. Therefore, bulk RI changes of the cover medium will induce a shift in the PWV, as will any thickness or density changes of a surface-bound biomolecular layer. Since bulk solution RI variations are a significant source of noise for surface-based optical biosensors, a higher ratio of surface-to-bulk sensitivity will consequently yield enhanced detection resolution. We therefore seek to maximize the PWV shift in response to a given biomolecular monolayer (i.e., a high surface shift coefficient for a medium of a particular index of refraction) while simultaneously limiting sensitivity to RI variations of the bulk media. In the example given here we use PPL (Poly-phe-lys) (Sigma-Aldrich; molecular weight=35,400 Daltons) to model the surface shift coefficient of a particular structure. PPL is a polymer thin film that conformally coats the sensor surface with a uniform monolayer of known refractive index material. We could have used any polymer or biological film of proteins or DNA that would stick to the surface of the biosensor for surface shift measurement.

In such optical biosensors, the evanescent electric field's interaction with the test sample determines the changes observed in the reflected optical spectrum due to changes in the dielectric permittivity, near the sensor surface. By modifying the device structure and hence the evanescent electric field profile, one can expect to change the sensitivity characteristics of the biosensor. Scaling down of the sensor structure will, for example, result in a related reduction in the extent of the evanescent fields. Also, the wavelength of resonance ($\lambda_r$) and the depth of penetration (d) of the evanescent field are linearly related by the equation, $d=\lambda_r/k$ where k is a constant for given angle of incidence of the incident illumination and the RI of the materials. Thus, by reducing the scale of the n-IR biosensor and enabling operation at lower wavelengths in the near ultraviolet, we expect to reduce the extent of the evanescent electric field significantly. Computer simulations using the Rigorous Coupled-Wave Analysis (RCWA) method for an optimized one-dimensional device geometry give the spatial profile of the electric field in the x-z plane for the n-UV and n-IR biosensors in FIGS. 5A and 5B, respectively.

The data for the n-IR device is used in this disclosure for comparison sake because the near-IR devices are well characterized and readily available and provide an example of a prior art biosensor arrangement. As will be explained below, the one-dimensional near-UV design provides an improvement of 4.5 in terms of the ratio surface sensitivity to bulk sensitivity as compared to the near-IR device.

Figure 5A:
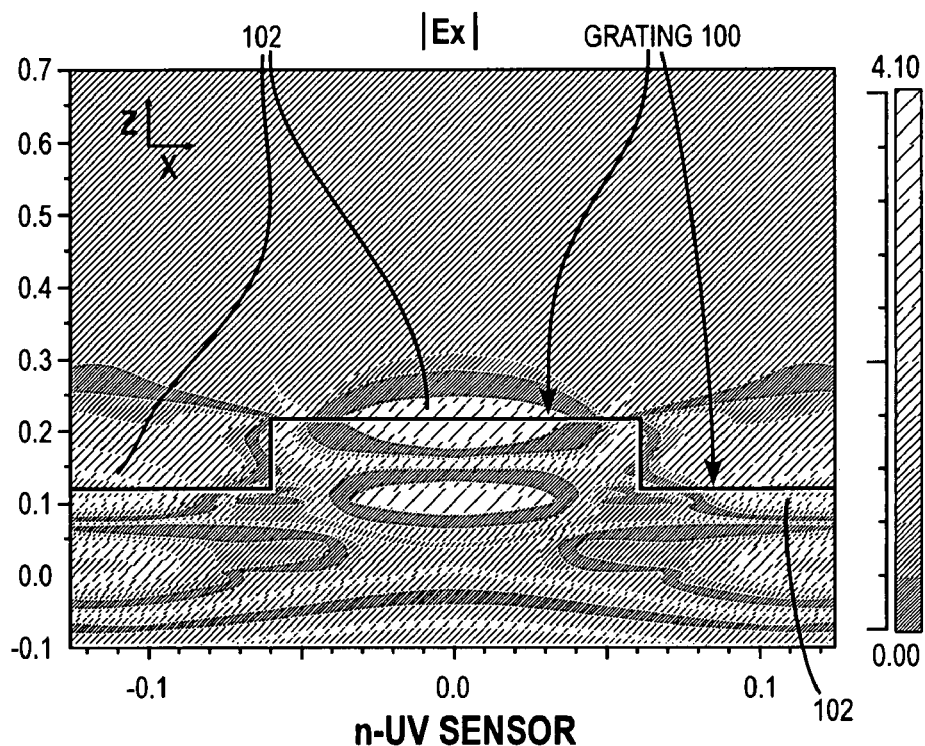
FIGS. 5A and 5B are Rigorous Coupled Wave Analysis (RCWA) simulations of resonant electric field profile for the n-UV biosensor (peak wavelength value (PWV) of reflected light having a maximum at λ=405 nm) (FIG. 5A) and n-IR biosensor (PWV having a maximum at λ=795 nm) (FIG. 5B). The field is clearly seen to be more tightly confined to the periodic surface grating structure of the n-UV biosensor, FIG. 5A. The plane-wave light source excites the structure from below along the z axis and has unit amplitude. The x and z axes indicate the extent of the simulation region.
Figure 5B:
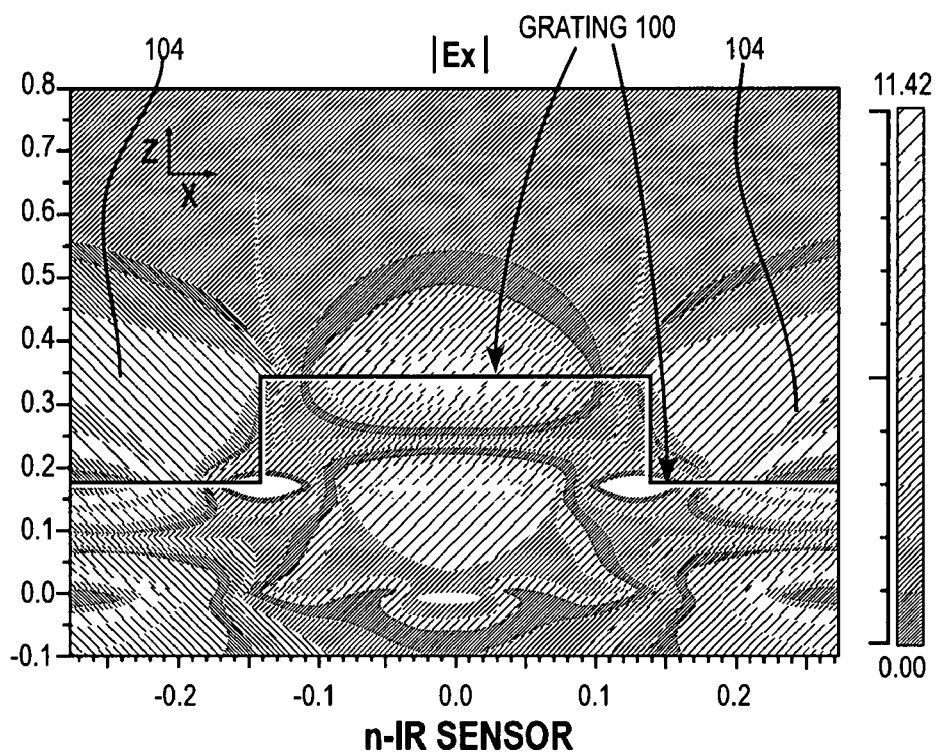

The plots of FIGS. 5A and 5B shows the electric field intensity profile for one period of the surface structure, for near-UV (FIG. 5A) and near IR (FIG. 5B) devices. The periodic boundary conditions are applied to the left and right limits and a grid size of 1 nm×1 nm is used. The incident illumination is TM polarized (i.e. the light is polarized perpendicular to the length of the surface structure) and is a plane-wave, incident from below the device. With respect to the scale shown in the figure, the plane-wave has unit amplitude. It is readily apparent that the field is more confined to the biosensor surface in the n-UV biosensor (FIG. 5A), and we can therefore expect changes in bulk refractive index to less dramatically tune the PWV. Note in particular the near-UV design has a more tightly confined resonant electric field at the surface of the grating (the stepped portion 100) as indicated at 102 in response to incident light at the surface of this biosensor as compared to previously fabricated near-infrared photonic-crystal biosensors (FIG. 5B, note the much larger and diffuse regions of electric field high intensity at 104, extending substantially above the surface of the grating 100).

The result of making the sensor structure with a substantially lower resonant wavelength in the near-UV is to decrease the spatial range of the evanescent electric field that extends vertically from the sensor surface and out into the test sample, as is clearly evident in FIG. 5A. Because the evanescent field is confined more closely to the sensor surface, a greater fraction of the field is within the first few (~5-50) nm, in which biomolecular attachment to the surface of the grating structure takes place. The field outside of this region only contributes to sensitivity to bulk refractive index changes. Accordingly, the tight confinement of the field to the surface as shown in FIG. 5A allows the biosensor to achieve the goal of having a high surface to bulk sensitivity ratio.

Figure 6A:
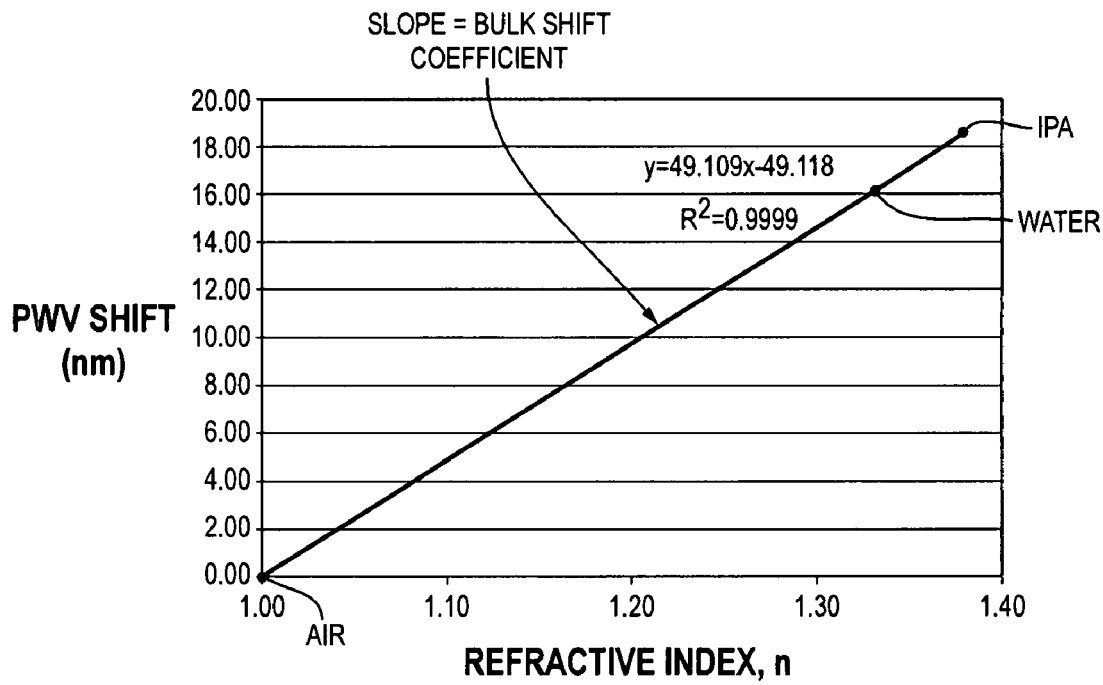
FIG. 6A is a graph of the experimental results of bulk shift coefficient measurement of the sensor of FIG. 4A. The bulk shift coefficient is calculated by the slope of the line (49.1 nm/RIU) that is obtained by plotting the PWV shift as the RI of the material at the surface of the biosensor is changed from air (RI=1) to that of water (RI=1.33) and IPA (RI=1.38)

To test the performance of the biosensor of FIG. 4A, the bulk-sensitivity was determined by measuring the change in PWV as the RI of the material covering the sensor varied. FIG. 6A shows the change of PWV for air, water and IPA applied to the sensor surface by placing a drop of each under a glass cover slip. The bulk-shift coefficient (defined as $\Delta PWV/\Delta n$ where n is the refractive index of the bulk medium) is given by the slope of this line and quantifies the bulk-sensitivity of the biosensor.

Figure 6B:
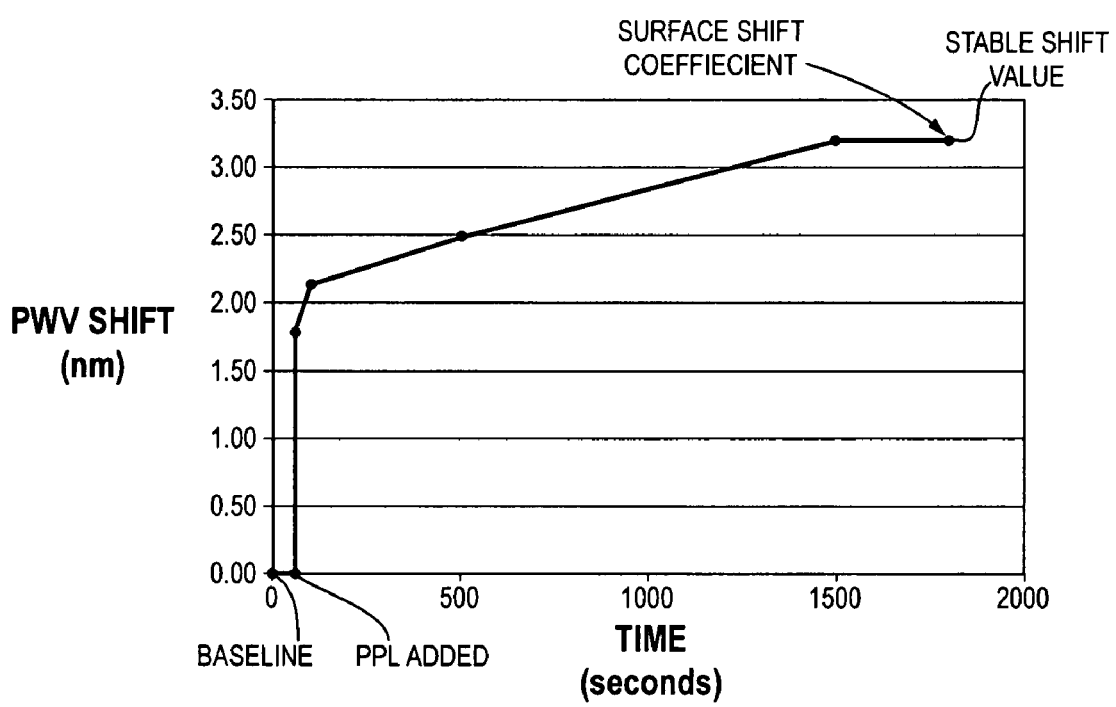
FIG. 6B is a graph of the experimental result of the surface sensitivity experiment for the near-UV biosensor of FIG. 4A. The maximum surface shift for a layer of PPL deposited at the biosensor surface is 3.19 nm.

Sensitivity to surface-adsorbed material (surface shift coefficient) is characterized by the detection of a single layer film of Poly(Lys, Phe) (PPL; Sigma-Aldrich; MW=35,400 Da) prepared to a 0.5 mg/ml solution with 0.01 M phosphate buffered saline (PBS; pH=7.4) applied to the sensor surface. The bioadhesion test commenced with the pipetting of PBS onto the sensor surface to establish a baseline PWV. After 10 min, the buffer was replaced with PPL solution and was allowed to stabilize for 30 min. The kinetics for this process is shown in FIG. 6B.

The highly confined electric field at the surface of the n-UV biosensors, as predicted by RCWA computer simulations of FIG. 4A, results in a very low bulk shift coefficient of 49.1 nm/RIU for the near-UV design of FIG. 4A. In contrast, the previously fabricated n-IR biosensors had a bulk shift coefficient of 302 nm/RIU.

The PWV change in response to a PPL monolayer deposited on the n-UV biosensor (i.e., surface shift coefficient) was measured to be 3.19 nm, whereas for the n-IR biosensors it has been previously measured to be 4.07 nm.

To provide a quantitative comparison of the surface-to-bulk sensitivity for the two biosensors, we divide the surface shift coefficient by the bulk shift coefficient, which results in the values 0.065 (3.19 divided by 49.1) and 0.013 (4.07 divided by 302) for the n-UV and n-IR biosensors respectively. This translates to an improvement of over 4.5 times for the surface-to-bulk sensitivity in the n-UV biosensor over the n-IR biosensor. Table 1 below summarizes these results.

TABLE 1

|  | n-IR biosensor | n-UV biosensor |
| --- | --- | --- |
| Reflection maximum (PWV) in air | 795 nm | 405 nm |
| Bulk Shift Coefficient | 302 nm/RIU | 49.1 nm/RIU |
| Maximum Surface Shift | 4.07 nm | 3.19 nm |
| Surface Shift/Bulk shift Coefficient | 0.013 | 0.065 |

Thus, as predicted, the strongly confined electric field at the surface of biosensors operating in a low wavelength regime serves to dramatically increase the surface-to-bulk sensitivity ratio. This figure of merit correlates directly with the PC biosensor's limit of detection. Therefore, the n-UV biosensor presented in this disclosure should enable improved biomolecular detection at low concentrations and is a significant step forward towards the ultimate goal of single molecule resolution.

Two-Dimensional Examples

The PC grating structure may take the form of a two-dimensional surface grating structure. The two-dimensional surface grating structure may comprises a two-dimensional array of posts or holes, arranged in a rectangular array, a hexagonal lattice, or other format. The posts or holes can have a variety of desired shapes, such as square, rectangular, circular, ovoid, triangular, etc. Examples of such 2D structures are shown in the published patent applications of SRU Biosystems cited in the background section of this document. See also PCT publication number WO 2007/019024.

Such a two-dimensional photonic crystal biosensor will typically take the form of an optically transparent substrate, and a relatively low index of refraction material formed in a periodic grating structure applied to the substrate. The low index of refraction material may optionally take the form of a porous dielectric material such as a spin-on glass such as Honeywell "NANOGLASS"™. A relatively high index of refraction material (e.g., $TiO_2$ or $Ti_2O_5$) is deposited onto the low index of refraction grating structure. The two-dimensional grating structure period and physical structure, and the thickness of the high index of refraction material, are selected such that the sensor produces a substantial confinement of the electric field intensity due to light directed to the biosensor substantially at the surface of the periodic grating, and will exhibit electric field profiles for example as shown in FIG. 5A. Furthermore, a reflection maximum at a resonant wavelength of the biosensor occurs in the near-ultraviolet portion of the spectrum (e.g., λ approximately in the range of 280-525 nm). Additionally, the biosensor grating structure and high and low index of refraction materials are selected to result in a biosensor which has a relatively high surface to bulk sensitivity ratio thereby improving the ability of the device to detect low concentrations of biomolecules, analytes, and/or and small molecules deposited on the surface of the biosensor.

Commercially available modeling software can be used to model field strength at the grating surface and arrive at appropriate dimensions, structures, periods, and thicknesses of two-dimensional structures meeting the objectives of this invention, such as R-Soft, available from RSoft Design Group, www.rsoftdesigngroup.com.

In any given two-dimensional design, the particular measurement of the bulk shift coefficient or the surface shift coefficient may vary from the values for the one-dimensional example above, however, it is contemplated that such 2D designs will obtain the significant improvements of surface to bulk shift ratio as achieved by the 1D design. For example, such two-dimensional biosensors may have a surface to bulk sensitivity ratio of approximately 0.060 or higher. Other 2D embodiments may have a bulk shift coefficient of approximately 100 nm/refractive index units (RIU) or less and a surface sensitivity coefficient measured from surface-absorbed material of PPL (poly-phe-lysine) of approximately 3 nm or greater.

Manufacturing Process

The biosensors of this disclosure can be in accordance with the following process.

First, a nanoreplication process is conducted by which a relatively low index of refraction material is patterned on an optically transparent substrate as a periodic surface grating structure. The example described above in the one-dimensional example is considered exemplary of both one- and two-dimensional biosensors. See also U.S. Pat. Nos. 7,297,298 and 7,162,125 for additional examples.

Next, a relatively high index of refraction material such as $TiO_2$ or $Ti_2O_5$ is deposited onto the periodic surface grating structure.

The resulting structure can be constructed in a web of material and then cut into sections, and affixed to other structures such as the bottom of a bottomless microtitre plate or other apparatus.

The grating structure period and high and low index of refraction materials are selected such that the sensor produces a substantial confinement of the electric field intensity due to light directed to the biosensor substantially at the plane of the periodic surface grating of the biosensor, such as shown in FIG. 5A, and the device exhibits a reflection maximum at a resonant wavelength in the near-ultraviolet portion of the spectrum. Additionally, the sensor grating structure period and high and low index of refraction materials are selected to result in a biosensor which has a relatively high surface to bulk sensitivity ratio thereby improving the ability of the device to detect low concentrations of biomolecules, analytes, and/or and small molecules deposited on the surface of the biosensor.

In one embodiment the step of coating the substrate with a relatively low refractive index of refraction material uses a porous glass. The method further includes the step of patterning the glass into a periodic grating structure with the aid of a stamp, also known as a grating master.

In one embodiment, the biosensors of this disclosure have a surface to bulk sensitivity ratio of approximately 0.060 or higher, calculated as explained above in the one-dimensional example.

In other embodiments, wherein the biosensor has a bulk shift ratio of approximately 50 nm/refractive index units (RIU) or less and has a sensitivity to surface-absorbed material of PPL (poly-phe-lysine) of approximately 3 nm or greater, where the bulk shift ratio is defined as the $\Delta PWV/\Delta n$, where $\Delta PWV$ is change in the resonance wavelength due to placement of a bulk medium on the surface of the biosensor, and where $\Delta n$ is the change in the refractive index due to the bulk medium applied to the surface of the biosensor.

Applications

In general, examples of specific binding substances (samples) which may be detected with the biosensor of this invention include nucleic acids, polypeptides, antigens, polyclonal antibodies, monoclonal antibodies, single chain antibodies (scFv), F(ab) fragments, F(ab')2 fragments, Fv fragments, small organic molecules, cells, viruses, bacteria, polymers, peptide solutions, protein solutions, chemical compound library solutions, single-stranded DNA solutions, double stranded DNA solutions, combinations of single and double stranded DNA solutions, RNA solutions and biological samples. Such biological samples could consists of, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears and prostatic fluid.

The biosensor described herein may be used to detect (a) binding of components any of these types of samples to the biosensor surface, (b) binding of the sample to another component of the sample, e.g., a fluorophore in the sample, and (c) binding of the sample or sample component to a second sample which is added to the sample. As an example of binding (b), the sensor surface may bind to some component of the sample, such as for example streptavidin-biotin or 6His, and the biosensor may be used to detect the interaction of the bound component of the sample with an additional grouping of components in the sample, such as a polymerase complex. In the latter example of binding (c), a sample may have a component that is attached to the surface of the biosensor and another component which specifically binds/attracts another component(s) from a second sample that is placed on the biosensor.

Detection System

In another aspect, a system for detection of low concentrations of biomolecules, analytes, and/or and small molecules can consist of the near-UV biosensor as described herein (either one dimensional or two dimensional), wherein the biomolecules, analytes and/or small molecules are deposited on the surface of the biosensor, and a detection instrument for illuminating the biosensor and measuring a shift in the peak wavelength value of reflected light from the surface of the biosensor, the shift in peak wavelength value due to the presence of the low concentration of the biomolecules, analytes and/or small molecules deposited on the surface of the biosensor. The detection system may take the form of the detection system shown in FIGS. 1 and 4A and described in the above-referenced patent literature of the co-assignee SRU Biosystems, Inc. Further examples of suitable detection instructions are disclosed in PCT publication number WO 2007/019024, the entire content of which is incorporated by reference herein.

While a number of exemplary aspects and embodiments have been discussed above, those of skill in the art will recognize certain modifications, permutations, additions and sub-combinations thereof as being present within the disclosure. It is therefore intended that the appended claims hereafter introduced are interpreted to include all such modifications, permutations, additions and sub-combinations as are within their true spirit and scope.

We claim:

1. A photonic crystal biosensor comprising:
   an optically transparent substrate,
   a relatively low index of refraction material formed in a periodic grating structure applied to the substrate, the relatively low index of refraction material comprising a porous dielectric material;
   a relatively high index of refraction material deposited onto the relatively low index of refraction material forming the grating structure;
   wherein the grating structure period and relatively high and low index of refraction materials are selected such that the sensor produces a confinement of the electric field intensity due to light directed to the biosensor proximate to the plane of the periodic surface grating of the biosensor and wherein a reflection maximum at a resonant wavelength of the biosensor occurs in the near-ultraviolet portion of the spectrum;
   and further wherein the sensor grating structure period and relatively high and low index of refraction materials are selected to result in a biosensor which has a high surface to bulk sensitivity ratio.

2. The biosensor of claim 1, wherein the biosensor has a surface to bulk sensitivity ratio of 0.060 or higher.

3. The biosensor of claim 1, wherein the biosensor has a bulk shift coefficient of 100 nm/refractive index units (RIU) or less and has a sensitivity to surface-absorbed material of PPL (poly-phe-lysine) of 3 nm or greater;
   where the bulk shift coefficient is defined as the $\Delta PWV/\Delta n$, where $\Delta PWV$ is change in the resonance wavelength due to placement of a bulk medium on the surface of the biosensor, and where $\Delta n$ is the change in the refractive index due to the bulk medium applied to the surface of the biosensor.

4. The biosensor of claim 1, wherein the grating structure comprises a one-dimensional surface structure.

5. The biosensor of claim 4, wherein a reflection maximum at a resonant wavelength of the biosensor occurs in the range of 280-525 nm.

6. The biosensor of claim 1, the grating structure comprises a two-dimensional surface grating structure.

7. The biosensor of claim 6, wherein the two-dimensional surface grating structure comprises a two-dimensional array of posts or holes.

8. A method of fabricating a highly sensitive biosensor comprising the steps of:
   a) conducting a nanoreplication process by which a relatively low index of refraction material is patterned on an optically transparent substrate as a periodic surface grating structure;
   b) depositing a relatively high index of refraction material onto the periodic surface grating structure;
   c) wherein the grating structure period and relatively high and low index of refraction materials are selected such that the sensor produces a confinement of the electric field intensity due to light directed to the biosensor proximate to the plane of the periodic surface grating of the biosensor and wherein a reflection maximum at a resonant wavelength occurs in the near-ultraviolet portion of the spectrum,
   d) and further wherein the sensor grating structure period and high and low index of refraction materials are selected to result in a biosensor which has a high surface to bulk sensitivity ratio.

9. The method of claim 8, wherein step a) comprises the step of coating the substrate with a relatively low refractive index porous glass, and patterning the glass into a periodic grating structure with the aid of a stamp.

10. The method of claim 8, wherein the biosensor has a surface to bulk sensitivity ratio of 0.060 or higher.

11. The method of claim 8, wherein the biosensor has a bulk shift coefficient of 100 nm/refractive index units (RIU) or less and has a sensitivity to surface-absorbed material of PPL (poly-phe-lysine) of 3 nm or greater;
   where the bulk shift coefficient is defined as the $\Delta PWV/\Delta n$, where $\Delta PWV$ is change in the resonance wavelength due to placement of a bulk medium on the surface of the biosensor, and where $\Delta n$ is the change in the refractive index due to the bulk medium applied to the surface of the biosensor.

12. The method of claim 8, wherein the grating structure comprises a one-dimensional surface structure and wherein the relatively low index of refraction material comprises a porous dielectric material.

13. The method of claim 12, wherein a reflection maximum at a resonant wavelength of the biosensor occurs in the range of 280-525 nm.

14. The method of claim 8, wherein the grating structure comprises a two-dimensional surface grating structure.

15. The method of claim 8, wherein the two-dimensional surface grating structure comprises a two-dimensional array of posts or holes.

16. A system for detection of low concentrations of biomolecules, analytes, or small molecules, comprising in combination:
   a biosensor according to claim 1, wherein the biomolecules, analytes or small molecules are deposited on the surface of the biosensor, and
   a detection instrument for illuminating the biosensor and measuring a shift in the peak wavelength value of reflected light from the surface of the biosensor, the shift in peak wavelength value due to the presence of the low concentration of the biomolecules, analytes or and/or small molecules deposited on the surface of the biosensor.

* * * * *